United States Patent [19]
Ohnmacht et al.

[11] Patent Number: 5,340,819
[45] Date of Patent: Aug. 23, 1994

[54] METHOD FOR TREATING URINARY INCONTINENCE USING 9-(3-NITROPHENYL)-3,4,6,7,9,10-HEXAHYDRO-1,8-(2H,5H) ACRIDINEDIONE

[75] Inventors: Cyrus J. Ohnmacht; Robert J. Harris; Diane A. Trainor, all of Wilmington, Del.

[73] Assignee: Imperial Chemical Industries plc, London, England

[21] Appl. No.: 963,863

[22] Filed: Oct. 20, 1992

[30] Foreign Application Priority Data

Oct. 21, 1991 [GB] United Kingdom ............... 9122305
Jun. 25, 1992 [GB] United Kingdom ............... 9213548

[51] Int. Cl.$^5$ ................................. A61K 31/435
[52] U.S. Cl. .................................. 514/297; 546/103
[58] Field of Search ................. 514/297; 546/103

[56] References Cited

U.S. PATENT DOCUMENTS

| | | | |
|---|---|---|---|
| 3,454,577 | 7/1969 | Lehr et al. | 546/103 |
| 3,901,710 | 8/1975 | Ranz et al. | |
| 4,021,434 | 5/1977 | Murakami et al. | 546/103 |
| 4,546,186 | 10/1985 | Abou-Gharbia | 546/102 |
| 5,258,390 | 11/1993 | Ohnmacht | 514/297 |

FOREIGN PATENT DOCUMENTS

| | | |
|---|---|---|
| 2003148 | 7/1971 | Fed. Rep. of Germany. |
| 2018738 | 10/1971 | Fed. Rep. of Germany. |
| 52-34631 | 9/1977 | Japan ............... 546/103 |
| 1575281 | 9/1980 | United Kingdom. |

OTHER PUBLICATIONS

A. H. Weston, T. C. Hamilton "Potassium Channel Modulators" *Frontiers in Pharmacology & Therapeutics* (1992), 462–485.
H. Hedlund, A. Mattiasson, K. E. Andersson "Effects of Pinacidil on Detrusor Instability in Men With Bladder Output Obstruction" *Journal of Urology* (1991), 146, 1345–1347.
S. Duty, A. H. Weston, "Potassium Channel Openers—Pharmacological Effects and Future Uses" *Drugs* (1990), 40, 785–791.
P. Zografos, et al. "Comparison of the in vitro Effects of K+ Channel Modulators on Detrusor and Portal Vein Strips from Guinea Pigs" *Pharmacology* (1992), 45, 216–230.
A. Malmgren, et al. "Effects of Cromakalim (BRL, 34915) and Pinacidil, on Normal and Hypertrophied Rat Detrusor in vitro" *The Journal of Urology* (1990), 143, 828–834.
A. Malmgren, et al. "Effects on Pinacidil and Cromakalim (BRL, 34915) on Bladder Function in Rats with Detrusor Instability" *The Journal of Urology* (1989), 142, 1134–1138.
A. Malmgren, et al. "Cystometrical Evaluation of Bladder Instability in Rats with Infravesical Outflow Obstruction" *The Journal of Urology* (1987), 137, 1291–1294.
C. D. Foster, et al. "The Effect of Cromakalim on the Smooth Muscle of the Guinea-pig Urinary Bladder" *British Journal of Pharmacology* (1989), 97, 281–291.
M. Fovaeus, et al. "The Action of Pinacidil in the Isolated Human Bladder" *The Journal of Urology* (1989), 141, 637–640.

(List continued on next page.)

*Primary Examiner*—Donald G. Daus
*Attorney, Agent, or Firm*—Robert J. Harris; Thomas E. Jackson; James T. Jones

[57] ABSTRACT

Compounds of general formula I,

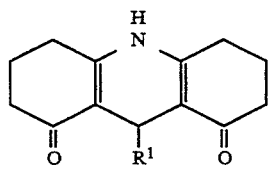

and pharmaceutically acceptable salts thereof, in which $R^1$ has any of the meanings given in the specification, pharmaceutical compositions comprising them and their use in the treatment of urinary incontinence.

1 Claim, No Drawings

OTHER PUBLICATIONS

K. Morikawa, et al. "Effects of Various Drugs on Bladder Function in Conscious Rats" *Japan. J. Pharmacol.* (1989), 50, 369–376.

C. A. Maggi, et al. "The Nonstop Transvestical Cystometrogram in Urethane-anesthesized Rats" *Journal of Pharmacological Methods* (1986), 15, 157–167.

D. E. Nurse et al. "The Effect of Cromakalim on the Normal and Hyperreflexic Human Detrusor Muscle" *British Journal of Urology*, (1991), 68, 27–31.

J. Restorik, D. Nurse "The effects of Cromakalim on Human Detrusor. An in vitro and in vivo Study" *Neurourology and Urodynamics* (1988), 7, 207–208.

S. M. Jain, et al. "Synthesis and Pharmacological screening of 1,8-dioxo-9-(substituted phenyl)-1, 2, 3, 4, 5, 6, 7, 8, 9, 10-decahydroacridines" *Ind. J. Chem.* (1991), 1037–1040.

H. Antaki "The Synthesis of Ethyl 4-Aryl-5,6,7,8-tetrahydro-5-oxoquinoline-3-carboxylates and their Derivatives" *J. Chem. Soc.* (1963), 4877–4879.

Ibrahim Chaaban, et al. "Enaminones in the Mannich Reaction. Part 2. Further Investigations of Internal Mannich Reactions" *J. Chem. Soc., Perkin I* (1979), 1593–1596.

Magid Abou-Gharbia "Synthesis of Novel Hexahydroquinolines and Hexahydroacridines" *Heterocycles* (1986), 24, 1347–1353.

A. H. Weston, T. C. Hamilton "Potassium Channel Modulators" *Frontiers in Pharmacology & Therapeutics* (1992), 462–485.

H. Hedlund, A. Mattiasson, K. E. Andersson "Effects of Pinacidil on Detrusor Instability in Men With Bladder Output Obstruction" *Journal of Urology* (1991), 146, 1345–1347.

METHOD FOR TREATING URINARY INCONTINENCE USING 9-(3-NITROPHENYL)-3,4,6,7,9,10-HEXAHYDRO-1,8-(2H,5H) ACRIDINEDIONE

This invention relates to compounds useful as cell potassium channel openers in mammals such as man. More specifically, the invention relates to certain 1,8-(2H,5H)-acridinediones which are useful in the treatment of urinary incontinence in mammals. Because compounds according to the invention function to open cell potassium channels, they may also be useful as therapeutic agents in the treatment of conditions or diseases in which the action of a therapeutic agent which opens potassium channels is desired or is known to provide amelioration. Such conditions or diseases include hypertension, asthma, peripheral vascular disease, right heart failure, congestive heart failure, angina, ischemic heart disease, cerebrovascular disease, renal cholic, disorders associated with kidney stones, irritable bowel syndrome, male pattern baldness, premature labor, and peptic ulcers.

DE 2003148 discloses a group of 1,4-dihydropyridine derivatives which are said to display a wide and multifaceted pharmacological spectrum of action. The main effects said to be displayed by the compounds include strong muscular spasmoytic effects which become evident in the smooth musculature of the gastrointestinal tract, of the urogenital tract and of the respiratory system. Other main effects are stated to be on the heart (a "heart-relieving" effect) and in reducing the blood pressure of normotonic and hypertonic animals, so that they can be used as antihypertensive agents.

S. M. Jain et al, Indian Journal of Chemistry, Volume 30B, November, 1991, pages 1037–1040 discloses the synthesis and pharmacological screening of certain 9-(substituted phenyl)-1,8-(2H,5H)-acridinediones. The compounds were found to possess varying degrees of hypotensive, anti-inflammatory and anti-implantation activities. One compound, 9-(3-nitrophenyl)-1,8-(2H,5H)acridinedione, which is also exemplified in DE 2003148, was found to display a marked hypotensive action when administered intravenously to dogs at a dose of 10 mg/kg.

It has now been found that certain of the 1,8-(2H,5H)acridinediones within the scope of the disclosure of DE 2003148, but not all of them, and certain other 1,8-(2H,5H)-acridinediones, are capable of relaxing bladder smooth muscle tissue.

This invention provides a compound of formula I (formula set out, together with other formulae referred to by Roman numerals, on pages following the Examples), or a pharmaceutically acceptable salt thereof, wherein:

$R^1$ is 1,2,3,4-tetrahydro-6-naphthyl, 1-naphthyl or 2-quinolyl; 2- or 3-thienyl or furyl substituted at the 4- and/or 5-position(s) by a substituent or substituents independently selected from nitro, cyano, halo, (1–4C)alkyl, (1–3C)alkylsulphonyl and 2-thienyl, provided that a 3-thienyl or furyl group may only be substituted at the 5-position; or a group of formula IV, wherein:

$R^2$ is hydrogen;

$R^3$ is selected from
(a) hydrogen, hydroxy and (1–4C)alkoxy;
(b) nitro, cyano, $CF_3$, $OCF_3$, halo, (1–4C)alkyl and (1–4C)alkanoyl;

$R^4$ is independently selected from the values in groups (a) and (b), phenyl, (1–3C)alkylsulphonyl and phenylsulfonyl, the phenyl rings of which may be substituted by 0–3 substituents selected from hydroxy, (1–4C)alkyl, (1–4C)alkoxy, halo, nitro, cyano, $CF_3$, $OCF_3$;

provided that if any of $R^3$ and $R^4$ is a value selected from (a), or if $R^4$ is (1–3C)alkylsulphonyl, at least one other value,
if for $R^3$, is selected from (b), or
if for $R^4$ is selected from (b) or is phenyl or phenylsulfonyl, the phenyl rings of which may be substituted by 0–3 substituents selected from hydroxy, (1–4C)alkyl, (1–4C)alkoxy, halo, nitro, cyano, $CF_3$, $OCF_3$;

and further provided that $R^1$ is not 5-nitro-2-furyl, 3-nitrophenyl, 4-nitrophenyl or 3-cyanophenyl.

The compounds of formula I wherein $R^1$ is 5-nitro-2-furyl, 3-nitrophenyl and 4-nitrophenyl are known, for example from DE 2718130, Antaki, J. Chem. Soc., 4877 (1963), U.S. Pat. No. 4,021,434, and DE 2003148.

The compound of formula I in which $R^1$ is 3-cyanophenyl is the subject of a co-pending patent application.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo" is inclusive of fluoro, chloro, bromo, and iodo unless noted otherwise.

Particular values of 2- or 3-thienyl or furyl substituted at the 4- and/or 5-positions include 4-bromo-2-thienyl, 5-bromo-2-thienyl, 5-methylsulphonyl-2-thienyl, 5-methyl-2-thienyl, 5-(2-thienyl)-2-thienyl, 4-nitro-2-thienyl, 5-nitro-2-thienyl, 4-cyano-2-thienyl, and 5-nitro-3-thienyl.

Particular values of (1–4C)alkyl include methyl, ethyl, propyl, isopropyl, butyl, isobutyl, sec-butyl, and tert-butyl.

Particular values of (1–3C)alkyl include methyl, ethyl, propyl, and isopropyl.

Particular values of (1–4C)alkoxy include methoxy, ethoxy propoxy, isopropoxy, butoxy, isobutoxy, sec-butoxy, and tert-butoxy.

Particular values of (1–4C)alkanoyl include ethanoyl.

Particular values of (1–3C)alkylsulphonyl include methanesulphonyl.

Particular values of phenylsulfonyl substituted with from 0–3 substitutents include phenylsulfonyl, 2-, 3-, and 4-hydroxyphenylsulfonyl, 2-, 3-, and 4-halophenylsulfonyl, 2-, 3-, and 4-cyanophenylsulfonyl, 2-, 3-, and 4-methylphenylsulfonyl, 2-, 3-, and 4-ethylphenylsulfonyl, 2-, 3-, and 4-propylphenylsulfonyl, 2 -, 3- and 4-methoxyphenylsulfonyl, 2-, 3-, and 4-ethoxyphenylsulfonyl, 2-, 3-, and 4-propoxyphenylsulfonyl, 2-, 3-, and 4-nitrophenylsulfonyl, 2-, 3-, and 4-trifluoromethylphenylsulfonyl, 2-, 3-, and 4-trifluoromethoxyphenylsulfonyl, 2,6-dichloro-4-nitrophenylsulfonyl, and 2,4-dimethyl-3-cyanophenylsulfonyl.

More particular values of phenylsulfonyl substituted with from 0–3 substitutents include those values of phenylsulfonyl substituted with 0–1 substituent, including phenylsulfonyl, 2-, 3-, and 4-hydroxyphenylsulfonyl, 2-, 3-, and 4-halophenylsulfonyl, 2-, 3-, and 4- cyanophenylsulfonyl, 2-, 3-, and 4-methylphenylsulfonyl, 2-, 3- and 4-methoxyphenylsulfonyl, 2-, 3-, and 4-nitrophenylsulfonyl, and 2-, 3-, and 4-trifluoromethylphenylsulfonyl.

More particular values of $R^3$ when selected from group (a) include hydrogen, hydroxy and methoxy.

More particular values of $R^3$ when selected from group (b) include nitro, cyano, trifluoromethyl, trifluoromethoxy, halo and ethanoyl.

More particular values of $R^4$ when selected from group (a) include hydrogen, hydroxy and methoxy.

More particular values of $R^4$ when selected from group (b) include nitro, cyano, trifluoromethyl, trifluoromethoxy, halo, methyl, ethyl, isopropyl and t-butyl. Of these, nitro, cyano, trifluoromethyl, trifluoromethoxy, halo, methyl and ethyl are particularly preferred.

Preferred compounds of formula I include those wherein $R^1$ is 1,2,3,4-tetrahydro-6-naphthyl, 1-naphthyl or 2-quinolyl; or 2- or 3-thienyl or furyl substituted at the 4- and/or 5-position(s) by a substituent or substituents selected from bromo, nitro, cyano, methyl, methanesulphonyl and 2-thienyl; or a group of formula IV wherein $R^2$ is hydrogen; $R^3$ is selected from hydrogen, hydroxy, nitro, cyano, halo, trifluoromethyl, trifluoromethoxy and ethanoyl; and $R^4$ is selected from hydrogen, hydroxy, methoxy, nitro, cyano, halo, trifluoromethyl, trifluoromethoxy, methyl, ethyl, isopropyl, tert-butyl, phenyl, methanesulphonyl and phenylsulfonyl.

A compound of formula I can be made by processes which include processes known in the chemical arts for the production of structurally analogous compounds. Such processes for the manufacture of a 1,8-(2H,5H)-acridinedione of formula I as defined above are provided as further features of the invention and are illustrated by the following procedures in which the meanings of generic radicals are as given above unless otherwise qualified. If not commercially available, the necessary starting materials for the processes such as those described following may be made by procedures which are selected from standard organic chemical techniques, techniques which are analogous to the synthesis of known, structurally similar compounds, or techniques which are analogous to the above described procedure or the procedures described in the examples. Such a process can be effected, generally, (a) by reacting a corresponding benzaldehyde of formula II, or an acetal or hemiacetal thereof, with ammonia or an ammonium salt (such as ammonium acetate) and 1,3-cyclohexanedione. The synthesis can be carried out along the lines reported by Abou-Gharbia in Heterocycles, 24 (5), 1347–1353, (1986), employing a corresponding substituted benzaldehyde in place of the heterocyclic aldehyde used therein. Suitable reaction conditions are also reported by Antaki in J. Chem. Soc., 4877 (1963).

(b) by reacting a compound of formula III with a corresponding benzaldehyde of formula II, or an acetal or hemiacetal thereof or a reactive derivative thereof. The reaction can be conducted as reported by Chaaban et al. in J. Chem. Soc. Perkin I, 1593 (1978), or by Eynde et al, Tetrahedron, Vol 48, No. 7, pp 1263–1268, 1992.

Reaction (a) is conveniently effected at a temperature in the range of from 0° to 100° C., preferably at an elevated temperature, for example in the range of from 35° to 90° C. Suitable solvents for the reaction include alcohols, for example, methanol or ethanol and carboxylic acids, for example acetic acid. The ammonia may, if desired, be employed in the form of ammonium hydroxide.

When benzaldehyde, or an acetal or hemiacetal thereof is used in reaction (b), the reaction is conveniently performed in the presence of an acid catalyst, for example hydrochloric acid, sulphuric acid, acetic acid or p-toluenesulphonic acid. Conveniently the reaction temperature is in the range of from 0° to 100° C., preferably from 25° to 40° C. Suitable solvents for the reaction include alcohols, for example ethanol.

When a reactive derivative of benzaldehyde is used in reaction (b), this may be, for example an N-(alpha-chlorophenylmethyl)pyridinium chloride. Thus, the benzaldehyde may be treated with thionyl chloride, and pyridine in the presence of a halogenated hydrocarbon solvent, such as dichloromethane, and the resultant N-(alpha-chlorophenylmethyl)pyridinium chloride may then be reacted with the compound of formula III.

It is noted that many of the starting materials for synthetic methods as described above are commercially available and/or widely reported in the scientific literature.

Pharmaceutically acceptable salts may be obtained using standard procedures well known in the art, for example by reacting a compound of formula I with a suitable acid or base affording a physiologically acceptable counterion.

When used to treat urinary incontinence, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a feature of the invention.

According to another aspect, therefore, the invention provides a pharmaceutical composition, which comprises a compound of formula I or a pharmaceutically acceptable salt thereof, as defined hereinabove, or a compound of formula I in which $R^1$ is 5-nitro-2-furyl or a pharmaceutically acceptable salt thereof, and a pharmaceutically acceptable diluent or carrier.

The compositions may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous, intravesicular, subcutaneous or intramuscular injection or infusion; or in the form of a patch for transdermal administration.

The invention further provides a method for the treatment of urinary incontinence, comprising administering to a mammal in need of such treatment an effective amount of a compound of formula I as defined above, or a compound of formula I in which $R^1$ is 5-nitro-2-furyl, 3-nitrophenyl or 4-nitrophenyl, or a pharmaceutically acceptable salt thereof.

It has surprisingly been found that the compound of formula I in which $R^1$ is 3-nitrophenyl [9-(3-nitrophenyl)-3,4,6,7,9,10-hexahydro-(2H,5H)-acridinedione] is capable of acting selectively on the bladder without at the same time appreciably or significantly affecting the cardiovascular system, as indicated by heart rate and blood pressure measurements. Thus, the compounds can advantageously be used to treat urinary incontinence in patients such as the elderly, for whom cardiovascular effects, such as a hypertensive effect, are particularly undesirable.

According to a preferred aspect, therefore, the invention provides a method for the treatment of urinary incontinence, comprising administering to a mammal in need of such treatment an effective amount of [9-(3-nitrophenyl)-3,4,6,7,9,10-hexahydro-(2H,5H)acridinedione or a pharmaceutically acceptable salt thereof.

Treatment using a compound according to the invention can be remedial or therapeutic as by administering a compound following the onset or development of urinary incontinence in a patient. Treatment can also be prophylactic or prospective by administering a compound in anticipation that urinary incontinence may develop, for example in a patient who has suffered from incontinence in the past.

According to a further aspect, the invention provides the use of a compound of formula I, as defined hereinabove, or a compound of formula I in which $R^1$ is 5-nitro-2-furyl, 3-nitrophenyl or 4-nitrophenyl in the manufacture of a medicament for the treatment of urinary incontinence.

It is known that bladder tissue is excitable and that urinary incontinence can be caused by uncontrolled or unstable bladder contractions. It is further known that by functioning to open potassium channels, potassium channel opening compounds can thereby function to relax smooth muscle. While not wishing to be bound by theory, it is accordingly believed that the compounds of this invention function by opening potassium channels in bladder cells and thereby relax bladder smooth muscle tissue, thus preventing or ameliorating uncontrolled bladder contractions which can cause urinary incontinence.

The dose of compound of formula I which is administered will necessarily be varied according to principles well known in the art taking account of the route of administration, the severity of the incontinence condition, and the size and age of the patient. In general, a compound of formula I will be administered to a warm blooded animal (such as man) so that an effective dose is received, generally a daily dose of above 0.005, for example in the range of about 0.01 to about 10 mg/kg body weight. Preferably the compound is administered orally in this dose range. It has been found that 9-(3-nitrophenyl)-3,4,6,7,9,10-hexahydro-(2H,5H)-acridinedione is active and selective in rats when administered orally at a dose of 3 mg/kg and 10 mg/kg. It will be appreciated that the precise dose range at which this compound may be dosed to obtain a selective effect will depend upon the particular species to be treated. This dose range may be determined by conventional methods. In general, it is expected that a selective effect will be obtained when the compound is dosed orally at 3 mg/kg or below, for example at 1 mg/kg or below.

It will be apparent to those skilled in the art that a compound of formula I can be co-administered with other therapeutic or prophylactic agents and/or medicaments that are not medically incompatible therewith. Compounds within the scope of the invention do not show any indication of untoward side-effects in laboratory test animals at several multiples of the minimum effective dose.

The actions of compounds of formula I as smooth muscle relaxants useful as therapeutic agents for the treatment of urinary incontinence can be shown using suitably designed in vitro tests, such as the one described following. Compounds according to the invention typically exhibit an $IC_{50}$ on the order of 30 micromolar or less in the test. For example, the compound of formula I in which $R^1$ is 3-nitrophenyl exhibits an $IC_{50}$ of 4.4±0.5 micromolar in the test, and the compound of formula I in which $R^1$ is 5-nitro-2-furyl, 2.1 micromolar. "$IC_{50}$" is a well understood term and means the concentration of test compound which causes a 50% decrease in the in vitro contraction of the bladder tissue described in the following test.

Male albino Hartley guinea pigs (450–500g) are sacrificed by cervical dislocation. The lower abdominal cavity is opened and the urinary bladder located. Once located, it is cleaned of surrounding connective and adipose tissue. The two pelvic nerves on the ventral surface of the bladder are cut away, then the bladder body is removed above the entrance of the ureters. The bladder is washed in Krebs-Henseleit buffer solution (composition (mM): NaCl 118.0, KCl 4.7, $MgSO_4$ 1.2, $KH_2PO_4$ 1.2, $CaCl_2$ 2.5, $NaHCO_3$ 25 and D-Glucose 11.1) and then placed on a buffer-soaked gauze in a petri dish. The dome of the bladder is cut off and discarded.

A mid-ventral longitudinal cut is made with scissors and the bladder laid flat on the gauze. Strips are cut from the dome edge and the base edge and discarded. The remaining detrusor mid-section is cut into two latitudinal (horizontal) strips, with an approximate width of 2.0 mm. These two strips are cut in half at the mid-dorsal section, creating four strips of similar dimensions. Each strip thus contains both dorsal and ventral portions of the bladder.

Each individual strip is tied at one end directly to a glass support rod and a length of 4-0 black braided silk suture is tied to the other end. The glass rods are secured in 20ml tissue baths and the length of suture attached to a force-displacement transducer (Grass model FT03).

The tissues are bathed in Krebs-Henseleit buffer solution. The bathing solution is warmed to 37° C. and gassed with 5% $CO_2$ and 95% $O_2$, with vigorous bubbling. The solution should have a pH value close to 7.4.

The transducers are connected to a polygraph (Grass model 7E) and interfaced with a Modular Instrument Micro 5000 signal processing system and Biowindow Data Acquisition Software (run on Microsoft OS/2 with an IBM-compatible PC)

The polygraph is calibrated at 5mV/cm and calibration checked for linearity with weights of 5 and 0.5 grams.

The tissue is incubated in the buffer for 15 minutes without preload tension, then 30 minutes with tension applied. The preload tension applied is 2 grams that relaxes to approximately 1 gram. The tissue is washed at 15 minute intervals, with tension adjusted to 2 grams just prior to washing. After this 45 minute equilibration period, a priming dose of 15mM KCl (total concentration in bath) is applied. The tissue is washed after 10 minutes and washed twice more at 15 minute intervals with tension adjusted to 2 grams before each washing.

When the tissue relaxes to a steady state after the final washing, 15mM KCl is again dosed. Once the tissue reaches a steady state the base line data are acquired on the Biowindows Data Acquisition System. This is done by averaging 5 minutes of data, sampling at 32 Hz. Once the baseline is acquired, the experimental compounds are dosed in a cumulative manner in half log unit increments. The contact time for each dose is 10 minutes with the final 5 minutes being the period of time that the dose response data are acquired. If 30 μM of the test compound does not abolish detrusor mechanical activity, then 30 μM cromakalim is dosed to establish a maximum response. The effects of the compounds are expressed as % of maximum relaxation of agonist induced tension.

It will be further appreciated by those skilled in the art that the efficacy of compounds according to the invention can be demonstrated by standard assays in vivo. The following is a description of such a standard test.

Male Wistar rats weighing 450–550 grams are anesthetized with 20 mg/kg, i.p. Nembutal and 80 mg/kg, i.p. Ketamine. The trachea is cannulated to prevent airway obstruction. Body temperature is maintained by means of a heating pad. Arterial blood pressure and heart rate may be measured with a pressure transducer connected to a polyethylene tube (PE50) which has been inserted into the right carotid artery. The right jugular vein is cannulated for drug administration. The urinary bladder is exposed through a midline abdominal incision and emptied of urine by application of slight manual pressure. A catheter (PE 50) is inserted through the apex of the bladder dome around 3–4 mm into its lumen and tied with suture (4-0 silk) to prevent leakage. The bladder catheter is connected to a pressure transducer for the measurement of bladder pressure. The bladder is then placed back into the abdominal cavity and the incision is stitched closed except where the catheter exits the cavity. The bladder is allowed to equilibrate for approximately 15 minutes. After the equilibration period, the rats are infused with saline directly into the bladder at a rate of 0.05 ml/min for the entire time of the experiment. The bladder pressure is then monitored for the start of bladder contractions. When the contractions start, the animal is then allowed to stabilize its pattern of contractions around 30 to 45 minutes before drug administration.

The test compounds are given i.v. The efficacy of a test compound is measured by comparison to the known reference drug cromakalim (SmithKline-Beecham) which is administered i.v. over the dose range of 0.05 to 0.5 mg/kg.

The above in vivo assay enables an assessment of both the blood pressure and cystometric activity of test compounds. Blood pressure is measured immediately after drug injection and at 5, 15 and 30 minutes later. Micturition contractions are induced by a slow continuous infusion of saline directly into the bladder. The average change (in seconds from control) in the duration of the intercontraction interval (the time between contractions) over an approximate 20-min period is reported for each compound.

The following is a description of a test in vivo which is complimentary to the above described tests and which can be used to ascertain if a test compound is active and, additionally, if the test compound exhibits selectivity for the bladder without significant cardiovascular effects when dosed orally. The compound of formula I in which $R^1$ is 3-nitrophenyl is active and selective in this test when dosed orally at 3mg/kg and 10mg/kg body weight.

Male Wistar rats (400–500 g) were anesthetized with 50 mg/kg Nembutal, i.p. For each rat, the abdominal region and the front and back of the neck were shaved and povidone-iodine was applied to the skin. For carotid catheterization, the left carotid artery was exposed via a small ventral cervical incision. The exposed area was flushed with a 2% lidocaine HCl solution to relax the vessel. The catheter, filled with 0.9% saline, was introduced approximately 2.4 cm into the artery so that its tip resided in the aortic arch. The distal end of the catheter was exteriorized at the nape of the neck, filled with heparin (1000 units/ml) and heat sealed. For bladder catheterization, the bladder was exposed through a midline abdominal incision. A trocar was passed through the abdominal muscle about 1 cm from the upper end of the incision and then tunneled subcutaneously to emerge through the skin at the back of the neck. A saline-filled catheter was passed through the trocar. A small opening in the bladder dome was created with an Accu-Temp cautery. The catheter was placed into the bladder and secured with a 4-0 silk ligature. The catheter was flushed with saline and patency was noted. The external end of the catheter was heat-sealed to prevent urine leakage. The abdominal muscles and the skin were sutured. Both catheters were threaded through a stainless steel anchor button (Instech), which was then sutured to the subcutaneous muscle at the point of exteriorization. The skin was sutured closed over the button. The animals were allowed to recover from anesthesia.

24–48 hours after surgery, each rat was placed in a metabolism cage and connected via the anchor button to an Instech spring tether and swivel system to protect the catheters from damage and to allow the animal free movement in the cage. The carotid catheter was connected to a Gould P23XL pressure transducer for blood pressure measurement. The bladder catheter was connected to a pump for saline infusion and to a pressure transducer by means of PE50 tubing and a 4-way stopcock. A toploading balance with a collection cup was placed under the cage for urine output measurement.

The rats were weighed, orally sham-dosed (dosing needle introduced, but no fluid expelled), and transvesical saline infusion (0.18 ml/min) was begun and continued throughout the experiment. Variations in blood pressure, heart rate, intravesical pressure and urine output were recorded on either a Grass Polygraph or a Gould TA4000 recording system. The animals were allowed to equilibrate until the micturition pattern became consistent (approx. 45–90 min.). At this point, a basal level of each experimental parameter was recorded and the rats were administered by oral garage the appropriate dose of compound (in a 75% PEG 400 - saline vehicle) in concentrations such that the volume was 1 ml/kg body weight. The effects of the compounds on experimental parameters were followed for five hours after administration.

Experimental results for both the interval between contractions and also heart rates were expressed as the mean ± S.E.M. (Standard Error of Measures) % change from basal level, with each animal serving as its own control. MAP is expressed as mean ± S.E.M mm Hg change from basal level.

It is further noted that the compound of formula I in which $R^1$ is 3-nitrophenyl also exhibits activity and selectivity when tested in vivo in a dog model.

Compounds according to the invention are active in one or more of the above-described tests.

The invention will now be illustrated by the following non-limiting examples in which, unless stated otherwise:

(i) temperatures are given in degrees Celsius (° C); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means 'flash chromatography' (method of Still) carried out on Merck Kieselgel (Art 9385 from E. Merck, Darmstadt, Germany), elution using both step and ramp gradients is denoted by the parenthetical term "gradient" followed by the initial and final solvent ratios; thin layer chomatography (TLC) was carried out on 0.25 mm silica gel GHLF plates (Art 21521 from Analtech, Newark, Del., USA);

(iv) in general, the course of reactions was followed by TLC and reaction times are given for illustration only;

(v) melting points are uncorrected; in general the materials melt with some decomposition; when it precedes a value for a melting point, the symbol ">" denotes "that the material melted at a temperature greater than the value shown;

(vi) final products had satisfactory nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 250 MHz using DMSO-$d_6$ as solvent; conventional abbreviations for signal shape are used; for AB spectra the directly observed shifts are reported; partial NMR data is reported for some products (ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the chemical ionizaton mode using a direct exposure probe; where indicated ionization was effected by electron impact (EI) or fast atom bombardment (FAB); generally, only peaks which indicate the parent mass are reported.

EXAMPLE 1

9-(3-Trifluoromethylphenyl)-3,4,6,7,9,10-hexahydro-1,8(2H,5H)-acridinedione.

A stirred mixture of 3-trifluoromethylbenzaldehyde (3.48 g), 1,3-cyclohexanedione (4.49 g), ammonium acetate (2.31 g) and ethanol (40 mL) was refluxed for 18 hours. The mixture was cooled and the yellow needles were collected, washed with water and dried in vacuo to give the title compound (6.38 g); mp >300 C; NMR: 1.7–2.0 (m,4), 2.19–2.25 (m,4), 2.50–2.56 (m,4), 4.98 (s,1), 7.41 (s,3), 7.48 (s,1), 9.48 (s,1); MS: m/z=362(M+1). Found for $C_{20}H_{18}F_3NO_2$: C, 66.44; H, 5.00; N, 3.80.

EXAMPLE 2

9-(4-Phenylsulfonylphenyl)-3,4,6,7,9,10-hexahydro-1,8-(2H,5H)acridinedione.

A stirred mixture of 4-phenylsulfonylbenzaldehyde (1.23 g), 1,3-cyclohexanedione (1.12 g), ammonium acetate (0.58 g) and ethanol (10 mL) was refluxed for 4 hours. The mixture was cooled and the light yellow crystals were collected, washed with water and dried in vacuo. A second crop obtained, by treatment of the liquors with water, was added to the dried solid and the total material was chromatographed with ether:methylene chloride as the eluent (20:80) followed by methanol:dichloromethane (10:90). Evaporation and recrystallization from ethanol:hexane yielded the title compound as a hemihydrate (1.10 g) as a pale yellow solid; mp 260° C.; NMR: 1.74–1.93 (m,4), 2.11–2.26 (m,4), 2.43–2.57 (m,4), 4.94 (s,1), 7.38 (d,2, J=8.3), 7.56–7.69 (m,3,), 7.77 (d,2, J=8.2), 7.93 (dd,2, J=8.3, 1.4), 9.53 (s,1,); MS: m/z=434(M+1). Found for $C_{25}H_{23}NO_4S \cdot 0.5\ H_2O$: C, 67.88; H, 5.37; N, 3.14.

EXAMPLES 3–41

Using a procedure similar to that described in Example 1, but substituting the requisite aldehyde for 3-trifluoromethylbenzaldehyde, the following compounds of Formula I in which $R^1$ is a group of Formula IV wherein $R^3$ and $R^4$ are the indicated groups were prepared.

EXAMPLE 3

$R^3$=nitro, $R^4$=chloro; mp >300° C.; NMR: 1.78–1.94 (m,4), 2.19–2.25 (m,4), 2.50–2.55 (m,4), 4.93 (s,1), 7.47 (dd,1, J=8.4, 2.1) 7.58 (d,1, J=8.3) 7.71 (d,1, J=2.0) 9.60 (s,1); MS: m/z=373(M+1). Found for $C_{19}H_{17}ClN_2O_4$: C, 61.20, H, 4.61; N, 7.49.

EXAMPLE 4

$R^3$=hydrogen, $R^4$=cyano; mp >300° C; NMR: 1.80–1.91 (m,4), 2.18–2.24 (m,4), 2.50–2.55 (m,4), 4.94 (s,1), 7.33 (d,2, J=8.2), 7.83 (d,2, J=8.2), 9.60 (s,1); MS: m/z=319(M+1). Found for $C_{20}H_{18}N_2O_2$: C, 75.13; H, 5.72; N, 9.00.

EXAMPLE 5

$R^3$=chloro, $R^4$=chloro; mp >300° C.; NMR: 1.7–2.0 (m,4) 2.25–2.5 (m,4) 2.9–3.2 (m,4) 4.87 (s,1) 7.11 (d,1, J=8.3) 7.32 (s,1) 7.43 (d,1, J=8.3) 9.56 (s,1); MS: m/z=362(M+1). Found for $C_{19}H_{17}Cl_2NO_2$: C, 62.82; H, 4.79; N, 3.63.

EXAMPLE 6

$R^3$=chloro, $R^4$=hydrogen; mp >300° C. Found for $C_{19}H_{18}ClNO_2$: C, 69.34; H, 5.57; N, 4.22.

EXAMPLE 7

$R^3$=trifluoromethoxyphenyl, $R^4$=hydrogen; mp 273–275° C. Found for $C_{20}H_{18}FNO_3$: C, 63.55; H, 4.71; N, 3.67.

EXAMPLE 8

$R^3$=hydrogen, $R^4$=trifluoromethoxyphenyl; mp 275°–276° C. Found for $C_{20}H_{18}F_3NO_3$: C, 63.53; H, 4.66; N, 3.66.

EXAMPLE 9

$R^3$=hydrogen, $R^4$=ethyl; NMR: 6.97 (d,2, J=8.0), 7.05 (d,2, J=8.0), 9.41 (s,1, NH); MS: m/z=322(M+1). Found for $C_{21}H_{22}NO_2$: C, 78.45; H, 7.20; N, 4.27.

EXAMPLE 10

$R^3$=iodo, $R^4$=hydrogen; mp 345°–347° C. Found for $C_{19}H_{18}INO_2$: C, 54.44; H, 4.37; N, 3.28.

EXAMPLE 11

$R^3$=acetyl, $R^4$=hydrogen; mp 288°–291° C. Found for $C_{21}H_{21}NO_3$: C, 75.07; H, 6.36; N, 4.12.

EXAMPLE 12

$R^3$=trifluoromethyl, $R^4$=methylsulfonyl; NMR: 7.65 (dd,1, J=8.2, J=1.4), 7.83 (d,1, J=1.4), 8.08 (d,1, J=8.2), 9.67 (s,1, NH); MS: m/z=440(M+1). Found for $C_{21}H_{19}NF_3O_2S$: C, 57.56; H, 4.63; N, 3.11.

EXAMPLE 13

$R^3$=trifluoromethyl, $R^4$=fluoro; mp 313°–316° C. Found for $C_{20}H_{17}F_4NO_2$: C, 63.28; H, 4.48; N, 3.61.

EXAMPLE 14

$R^3$=fluoro, $R^4$=hydrogen; NMR: 6.64–7.00 (m,3), 7.18–7.25 (m,1), 9.49 (s,1, NH); MS: m/z=312(M+1). Found for $C_{19}H_{18}NFO_2$: C, 73.30; H, 5.87; N, 4.37.

EXAMPLE 15

$R^3$=hydrogen, $R^4$=fluoro; NMR: 6.93–7.00 (m,2), 7.13–7.19 (m,2), 9.47 (s,1, NH); MS: m/z=312(M+1). Found for $C_{19}H_{18}NFO_2$: C, 72.90; H, 5.70; N, 4.22.

EXAMPLE 16

$R^3$=cyano, $R^4$=chloro; mp 293°–295° C. Found for $C_{20}H_{17}ClN_2O_2 \cdot 0.4 H_2O$: C, 66.46; H, 4.84; N, 7.76.

EXAMPLE 17

$R^3$=nitro, $R^4$=hydroxy; NMR: 6.96 (d,1, J=8.1), 7.32 (dd,1, J=8.1, J=1.7), 7.58 (d,1, J=11.7), 9.52 (s,1); MS: m/z=355(M+1). Found for $C_{19}H_{18}N_2O_5$: C, 64.42; H, 5.10; N, 7.83.

EXAMPLE 18

$R^3$=hydrogen, $R^4$=bromo; NMR: 7.10 (m,2), 7.33 (m,2), 9.49 (s,1, NH). Found for $C_{19}H_{18}NBrO_2$: C, 60.96; H, 4.83; N, 3.44.

EXAMPLE 19

$R^3$=hydrogen, $R^4$=iodo; NMR: 6.96 (m,2), 7.50 (m,2), 9.47 (s,1, NH). Found for: C, 54.05; H, 4.26; N, 3.22.

EXAMPLE 20

$R^3$=hydrogen, $R^4$=isopropyl; NMR: 1.13 (d,3, J=6.93), 2.76 (m,1), 7.04 (m,4), 9.41 (s,1); MS: m/z=336 (M+1). Found for $C_{22}H_{25}NO_2$: C, 78.42; H, 7.41; N, 4.10.

EXAMPLE 21

$R^3$=fluoro, $R^4$=fluoro; NMR: 6.95–7.26 (m,3), 9.54 (s,1, NH); MS: m/z=330(M+1). Found for $C_{19}H_{17}NF_2O_2$: C, 69.00; H, 5.13; N, 4.26.

EXAMPLE 22

$R^3$=chloro, $R^4$=methoxy; NMR: 6.93 (d,1, J=7.1), 7.03 (dd,1, J=7.1, J=1.7), 7.14 (d,1, J=1.7), 9.46 (s,1, NH); MS: m/z=358(M+1). Found for $C_{20}H_{20}NClO_3$: C, 66.78; H, 5.65; N, 3.78.

EXAMPLE 23

$R^3$=nitro, $R^4$=cyano; mp 298°–300°+ C. Found $C_{20}H_{17}N_3O_4$: C, 65.87; H, 4.78; N, 11.48.

EXAMPLE 24

$R^3$=nitro, $R^4$=bromo; NMR: 7.37–7.40 (m,1), 7.66–7.70 (m,2), 9.61 (s,1, NH); MS: m/z=417(M+1). Found for $C_{19}H_{17}N_2BrO_4$: C, 54.57; H, 4.00; N, 6.65.

EXAMPLE 25

$R^3$=hydrogen, $R^4$=phenyl; NMR: 7.22–7.59 (m,9), 9.48 (s,1); MS: m/z=370(M+1). Found for $C_{25}H_{23}NO_2$: C, 81.03; H, 6.29; N, 6.67.

EXAMPLE 26

$R^3$=fluoro, $R^4$=bromo; mp 308°–310° C. Found for $C_{19}H_{17}BrFNO_2$: C, 58.31; H, 4.42; N, 3.58.

EXAMPLE 27

$R^3$=chloro, $R^4$=bromo; mp 327°–330° C. Found for $C_{19}H_{17}BrClNO_2$: C, 56.21; H, 4.28; N, 3.40.

EXAMPLE 28

$R^3$=nitro, $R^4$=ethyl; NMR: 7.33(d,1, J=8.0), 7.43 (dd,1, J=8.0, J=1.6), 7.64 (d,1, d=1.6); MS: m/z=367(M+1). Found for $C_{21}H_{22}N_2O_4$: C, 68.76; H, 6.02; N=7.57.

EXAMPLE 29

$R^3$=trifluoromethyl, $R^4$=cyano; mp 289°–291° C. Found for $C_{21}H_{17}F_3N_2O_2$: , C, 65.08; H, 4.40; N, 7.22.

EXAMPLE 30

$R^3$=bromo, $R^4$=fluoro; mp 328°–331° C. Found for $C_{19}H_{17}BrFO_2$: C, 58.05; H, 4.44; N, 3.50.

EXAMPLE 31

$R^3$=nitro, $R^4$=phenylsulfonyl; NMR: 7.66–7.95 (m,7), 8.21 (d,1, J=7.9); MS=m/z=479(M+1). Found for $C_{25}H_{22}N_2O_6S$: C, 62.63; H, 4.76; N, 5.69.

EXAMPLE 32

$R^3$=methyl, $R^4$=hydrogen; mp 374°–378° C. Found for $C_{20}H_{21}NO_2$: C, 78.17; H, 6.93; N, 4.55.

EXAMPLE 33

$R^3$=trifluoromethyl, $R^4$=phenylsulfonyl; Dried at 100° C. under vacuum 3d. NMR: 7.59–7.87 (m,7), 8.25 (d,1, J=8.26); MS: m/z=502(M+1). Found for $C_{26}H_{22}NF_3O_4S$: C, 62.34; H, 4.54; N, 2.82.

EXAMPLE 34

$R^3$=hydrogen, $R^4$=tert-butylphenyl; mp >320° C. Found for $C_{23}H_{27}NO_2$: C, 79.13; H, 7.88; N, 3.93.

EXAMPLE 35

$R^3$=hydrogen, $R^4$=methyl; mp 311°–314° C. Found for $C_{20}H_{21}NO_2$: C, 78.23; H, 6.99; N, 4.50.

EXAMPLE 36

$R^3$=nitro, $R^4$=methyl; mp >310° C. Found for $C_{20}H_{20}N_2O_4$: C, 68.27; H, 5.71; N, 7.92.

EXAMPLE 37

$R^3$=hydrogen, $R^4$=trifluoromethyl; mp 273°–277° C. Found for $C_{20}H_{18}F_3NO_2$: C, 66.17; H, 5.01; N, 3.78.

EXAMPLE 38

$R^3$=chloro, $R^4$=fluoro; mp 325°–328° C. Found for $C_{19}H_{17}ClFNO_2$: C, 65.78; H, 4.88; N, 3.98.

EXAMPLE 39

$R^3$=bromo, $R^4$=hydrogen; mp 336°–339° C. Found for $C_{19}H_{18}BrNO_2$: C, 61.12; H, 4.94; N, 3.64.

EXAMPLE 40

$R^3$=hydrogen, $R^4$=chloro; mp >300° C. Found for $C_{19}H_{18}ClNO_2$: C, 69.35; H, 5.62; N, 4.11.

EXAMPLE 41

$R^3$=hydroxy, $R^4$=nitro; mp >375° C. Found for $C_{19}H_{18}N_2O_5 \cdot 0.5\ H_2O$: C, 62.74; H, 5.26; N, 7.53.

EXAMPLES 42–50

Using a procedure similar to that described in Example 1, but substituting the requisite aldehyde for 3-trifluoromethylbenzaldehyde, the following compounds of Formula I wherein $R^1$ is the indicated group were prepared.

EXAMPLE 42

$R^1$=5-bromo-2-thienyl; mp 281°–284° C. Found for $C_{17}H_{16}NBrO_2S$: C, 53.81; H, 4.22; N, 3.50.

EXAMPLE 43

$R^1$=4-bromo-2-thienyl; mp 322°–324° C. Found for $C_{17}H_{16}NBrO_2S$: C, 54.09; H, 4.33; N, 3.70.

EXAMPLE 44

$R^1$=5-methylsulfonyl-2-thienyl; mp 268° C. Found for $C_{18}H_{19}NO_4S_2$: C, 57.21; H, 5.09; N, 3.65.

EXAMPLE 45

$R^1$=1,2,3,4-tetrahydro-6-naphthyl; mp 332° C. Found for $C_{23}H_{25}NO_2$: C, 79.71; H, 7.35; N, 3.94.

EXAMPLE 46

$R^1$=1-naphthyl; mp 335° C. Found for $C_{23}H_{21}NO_2$: C, 80.41; H, 6.28; N, 4.06.

EXAMPLE 47

$R^1$=2-quinolyl; mp 290°–295° C. Found for $C_{22}H_{20}N_2O_2$: C, 76.42; H, 5.88; N, 7.75.

EXAMPLE 48

$R^1$=5-methyl-2-thienyl; mp 284°–285° C. Found for $C_{18}H_{19}NO_2S$: C, 68.74; H, 6.30; N, 4.38.

EXAMPLE 49

$R^1$=5-(2-thienyl)-2-thienyl; mp 249°–252° C. Found for $C_{21}H_{19}NO_2S_2$: C, 65.91; H, 5.06; N, 3.63.

EXAMPLE 50

$R^1$=5-nitro-3-thienyl; mp 273°–277° C. Found for $C_{17}H_{16}N_2O_4S$: C, 58.83; H, 4.75; N, 8.07.

EXAMPLE 51

9-(5-Nitro-2-thienyl)-3,4,6,7,9,10-hexahydro-1,8-(2H,5H)-acridinedione.

A stirred mixture of 3-amino-2-cyclohexen-1-one (1.38 g) and ethanol (8 mL) was treated with 1N hydrochloric acid (10 mL) to yield a clear solution. 5-Nitro-2-thiophenecarboxaldehyde (1.00 g) was added and the mixture stirred overnight. The resulting yellow solid was collected by suction filtration, washed with ethanol and dried under vacuum to yield the title acridinedione (1.40 g); mp 294°–7° C.; NMR: 1.82–2.00 (m,4, $CH_2$), 2.25–2.33 (m,4, $CH_2$), 2.47–2.56 (m,4, $CH_2$), 5.17 (s,1, CH) 6.77 (d,1, J=4.3) 7.85 (d,1, J=4.2), 9.80 (s,1, NH); MS: m/z=345(M+1). Found for $C_{17}H_{16}N_2O_4S$: C, 59.31; H, 4.75; N, 8.01.

EXAMPLES 52–54

Using a procedure similar to that described in Example 51, but substituting the requisite aldehyde for 5-nitro-2-thiophenecarboxaldehyde, the following compounds of Formula I wherein $R^1$ is the indicated group were prepared.

EXAMPLE 52

$R^1$=4-nitro-2-thienyl; mp 240° C. Found for $C_{17}H_{16}N_2O_4S$: C, 58.89; H, 4.69; N, 7.98.

EXAMPLE 53

$R^1$=4-cyano-2-thienyl; mp 296°–299° C. Found for $C_{18}H_{16}N_2O_2S \cdot 0.25 CH_2Cl_2$: C, 63.28; H, 4.99; N, 7.78.

EXAMPLE 54

$R^1$=5-nitro-2-furanyl; mp 293°–296° C. Found for $C_{17}H_{16}N_2O_5$: C, 61.95; H, 4.96; N, 8.41.

EXAMPLE 55

The following illustrate representative pharmaceutical dosage forms containing a compound of formula I, for example as illustrated in any of the previous Examples, (hereafter referred to as "compound X"), for therapeutic or prophylactic use in humans:

|  | mg/tablet |
|---|---|
| (a) Tablet | |
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |
| (b) Capsule | |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

FORMULAE

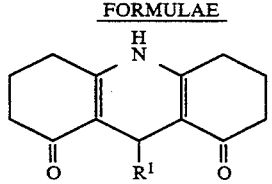

I

-continued
FORMULAE
  II
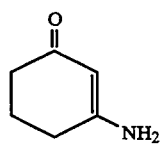  III
-continued
FORMULAE
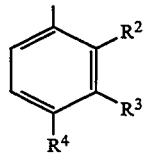  IV
We claim:
1. A method for the treatment of urinary incontinence, comprising administering to a mammal in need of such treatment an effective amount of the compound 9-(3-nitrophenyl)-3,4,6,7,9,10-hexahydro-1,8-(2H,5H)acridinedione.
* * * * *

UNITED STATES PATENT AND TRADEMARK OFFICE
CERTIFICATE OF CORRECTION

PATENT NO. : 5,340,819

DATED : August 23, 1994

INVENTOR(S) : Cyrus J. Ohnmacht

It is certified that error appears in the above-identified patent and that said Letters Patent is hereby corrected as shown below:

Title page, item:

[19], "Ohnmacht et al." should read --Cyrus J. Ohnmacht--.

[75], "Cyrus J. Ohnmacht; Robert J. Harris; Diane A. Trainor, all of Wilmington, Del." should read --Cyrus J. Ohnmacht, of Wilmington, DE--.

[56], "5,258,390" should read --5,238,390--.

UNITED STATES PATENT AND TRADEMARK OFFICE
CERTIFICATE OF CORRECTION

PATENT NO. : 5,340,819
DATED : August 23, 1994
INVENTOR(S) : Cyrus J. Ohnmacht

It is certified that error appears in the above-indentified patent and that said Letters Patent is hereby corrected as shown below:

Title page,
page 2, item [56], delete the following publications as they are duplicated:

1) A. H. Weston, T. C. Hamilton "Potassium Channel Modulators" Frontiers in Pharmacology & Therapeutics (1992), 462-485.

2) H. Hedlund, A. Mattiasson, K. E. Andersson "Effects of Pinacidil on Detrusor Instability in Men With Bladder Output Obstruction" Journal of Urology (1991), 146, 1345-1347.

Signed and Sealed this

Twenty-fifth Day of April, 1995

Attest:

BRUCE LEHMAN

Attesting Officer    Commissioner of Patents and Trademarks